(12) United States Patent
Burton

(10) Patent No.: US 9,757,716 B2
(45) Date of Patent: Sep. 12, 2017

(54) SYNTHESIS OF ZSM-5

(71) Applicant: ExxonMobil Chemical Patents Inc., Baytown, TX (US)

(72) Inventor: Allen W. Burton, Stewartsville, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/648,476

(22) PCT Filed: Nov. 22, 2013

(86) PCT No.: PCT/US2013/071446
§ 371 (c)(1),
(2) Date: May 29, 2015

(87) PCT Pub. No.: WO2014/099261
PCT Pub. Date: Jun. 26, 2014

(65) Prior Publication Data
US 2015/0328627 A1    Nov. 19, 2015

Related U.S. Application Data

(60) Provisional application No. 61/740,917, filed on Dec. 21, 2012.

(30) Foreign Application Priority Data

Feb. 19, 2013  (EP) ................................. 131557217

(51) Int. Cl.
| | | |
|---|---|---|
| *B01J 29/40* | (2006.01) | |
| *B01J 37/00* | (2006.01) | |
| *B01J 37/08* | (2006.01) | |
| *B01J 35/02* | (2006.01) | |
| *C07D 207/06* | (2006.01) | |
| *C01B 37/02* | (2006.01) | |
| *C01B 39/12* | (2006.01) | |
| *C01B 39/38* | (2006.01) | |
| *C01B 39/40* | (2006.01) | |
| *C07D 295/037* | (2006.01) | |

(52) U.S. Cl.
CPC ............... *B01J 29/40* (2013.01); *B01J 35/02* (2013.01); *B01J 37/0018* (2013.01); *B01J 37/082* (2013.01); *C01B 37/02* (2013.01); *C01B 39/12* (2013.01); *C01B 39/38* (2013.01); *C01B 39/40* (2013.01); *C07D 207/06* (2013.01); *C07D 295/037* (2013.01)

(58) Field of Classification Search
CPC ................................. B01J 35/02; B01J 29/40
See application file for complete search history.

(56) References Cited

U.S. PATENT DOCUMENTS

| | | |
|---|---|---|
| 3,702,886 A | 11/1972 | Argauer et al. |
| RE29,948 E | 3/1979 | Dwyer et al. |
| 4,585,638 A | 4/1986 | Kühl |
| 6,027,707 A | 2/2000 | Casci et al. |

FOREIGN PATENT DOCUMENTS

| | | |
|---|---|---|
| CN | 102442686 | 5/2012 |
| WO | 2010/065319 | 6/2010 |

OTHER PUBLICATIONS

Jackowski et al., "Diquaternary Ammonium Compounds in Zeolite Synthesis: Cyclic and Polycyclic N-Heterocycles Connected by Methylene Chains," J. Am. Chem Soc. (2009) 131, pp. 1092-1100.
Parikh et al., "Non-thermal calcination by ultraviolet irradiation in the synthesis of microporous materials," Microporous and Mesoporous Materials, Elsevier Publishers, 76 (2004) pp. 17-22.
Periodic Table of the Elements, Chemical & Engineering News vol. 63, No. 5 (1985) p. 27.

*Primary Examiner* — Shawquia Jackson
(74) *Attorney, Agent, or Firm* — Darryl M. Tyus

(57) ABSTRACT

A molecular sieve having the framework structure of ZSM-5 is produced using one or more of 1,4-bis(N-pentylpyrrolidinium)butane dications, 1,5-bis(N-pentylpyrrolidinium) pentane dications, and 1,6-bis(N-pentylpyrrolidinium) hexane dications as a structure directing agent.

7 Claims, 12 Drawing Sheets ized form, comprising one or more of 1,4-bis(N-pentylpyrrolidinium)butane dications, 1,5-bis(N-pentylpyrrolidinium)pentane dications, and 1,6-bis(N-pentylpyrrolidinium)hexane dications in its pores.

SYNTHESIS OF ZSM-5

CROSS REFERENCE TO RELATED APPLICATIONS

The present application is a National Stage Application of International Application No. PCT/US2013/071446, filed 22 Nov. 2013, and claims priority to and the benefit of U.S. Provisional Application No. 61/740,917 filed on 21 Dec. 2012, and claims priority to EP 13155721.7, filed 19 Feb. 2013, which are hereby incorporated by reference in their entireties.

FIELD

This invention relates to the synthesis of ZSM-5, and to the use of the resultant ZSM-5 as an adsorbent and a catalyst for organic conversion reactions.

BACKGROUND

Crystalline ZSM-5, and its conventional preparation using tetrapropylammonium cations as a structure directing agent, are taught by U.S. Pat. No. 3,702,886 and U.S. Pat. No. Re. 29,948, the entire disclosures of which are incorporated herein by reference. Conventional ZSM-5 has a distinctive X-ray diffraction pattern which distinguishes it from organic conversion reactions.

In addition to tetrapropylammonium cations, a large number of other organic nitrogen compounds, including certain diquaternary ammonium compounds, have been shown to direct the synthesis of ZSM-5. For example, U.S. Pat. No. 4,585,638 discloses that the synthesis of ZSM-5 can be directed by the diquaternary cation $(alkyl)_3N^+(CH_2)_6N^+(alkyl)_3$, where the alkyl group is propyl or butyl.

According to the present invention, it has now been found that ZSM-5 can be synthesized using certain novel bis(N-pentylpyrrolidinium)-diquat-n cations, where n=4, 5 or 6, as a structure directing agent. The ZSM-5 can be made across a wide range of Si/Al ratios (infinity to 12) and, in some cases, it has been found that novel ultra-small forms of ZSM-5 can be produced.

SUMMARY

In one aspect, the invention resides in a process for producing a molecular sieve having the framework structure of ZSM-5, the process comprising:

(i) preparing a synthesis mixture capable of forming said molecular sieve, said synthesis mixture comprising a source of an alkali or alkaline earth metal (M), a source of an oxide of a tetravalent element Y, optionally a source of a trivalent element X, water, and a directing agent (Q) comprising one or more of 1,4-bis(N-pentylpyrrolidinium)butane dications, 1,5-bis(N-pentylpyrrolidinium)pentane dications, and 1,6-bis(N-pentylpyrrolidinium)hexane dications, and said synthesis mixture having a composition, in terms of mole ratios, within the following ranges:

| | |
|---|---|
| $YO_2/X_2O_3$ | at least 20; |
| $H_2O/YO_2$ | 10 to 60; |
| $OH^-/YO_2$ | 0.20 to 0.60; |
| $M/YO_2$ | 0.05 to 0.40; and |
| $Q/YO_2$ | 0.05 to 0.20; |

(ii) heating said synthesis mixture under crystallization conditions, including a temperature of from 80° C. to 200° C., and a time from 1 day to 21 days until crystals of said molecular sieve are formed; and (iii) recovering said molecular sieve from step (ii).

In a further aspect, the invention resides in a molecular sieve having the structure of ZSM-5 and, in its as-synthesized form, comprising one or more of 1,4-bis(N-pentylpyrrolidinium)butane dications, 1,5-bis(N-pentylpyrrolidinium)pentane dications, and 1,6-bis(N-pentylpyrrolidinium)hexane dications in its pores.

Conveniently, the molecular sieve has a composition comprising the molar relationship:

$$(q)Q:X_2O_3:(n)YO_2$$

wherein $0<q/n\leq0.05$, n is at least 20, and Q, X and Y have the meanings indicated above.

In yet a further aspect, the invention resides in a process for converting a feedstock comprising an organic compound to a conversion product which comprises contacting said feedstock at organic compound conversion conditions with a catalyst comprising an active form of the molecular sieve described herein.

In still yet a further aspect, the invention resides in an organic nitrogen compound comprising a dication having one of the following formulae:

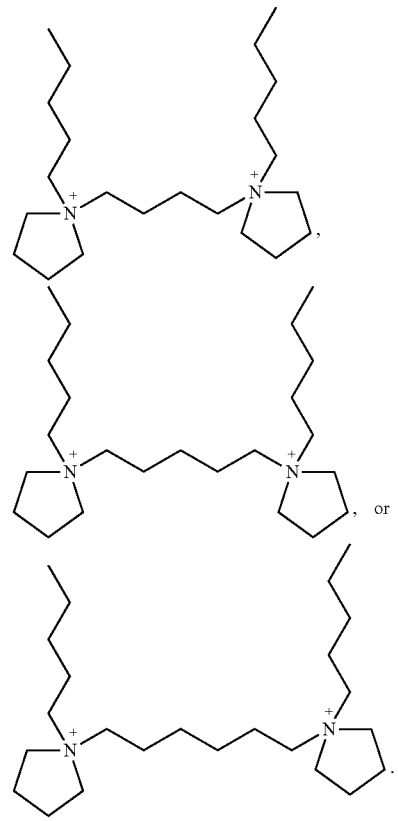

DETAILED DESCRIPTION OF THE EMBODIMENTS

Figure 1:
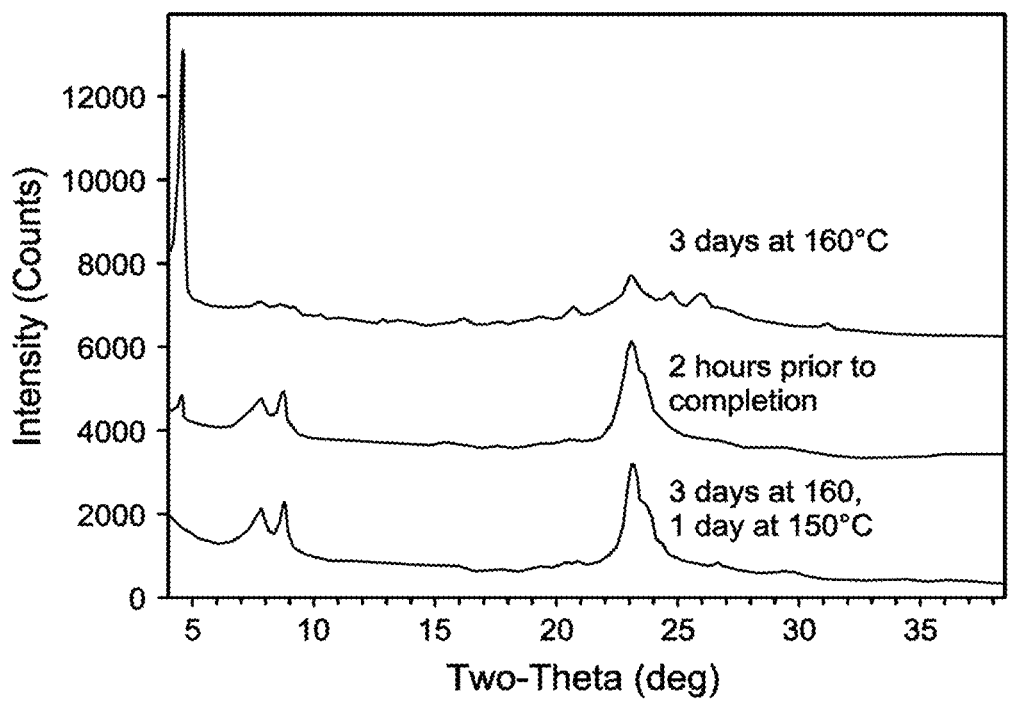
FIG. 1 compares the X-ray diffraction patterns of the as-synthesized product of Example 2 after crystallization for 3 days (top pattern), 3 days and 22 hours (middle pattern), and 4 days (bottom pattern).

Described herein is a process for the synthesis of ZSM-5 using one or more of the following novel diquaternary ammonium compounds as a structure directing agent:

(a) 1,4-bis(N-pentylpyrrolidinium)butane dications, which can be represented by the following formula:

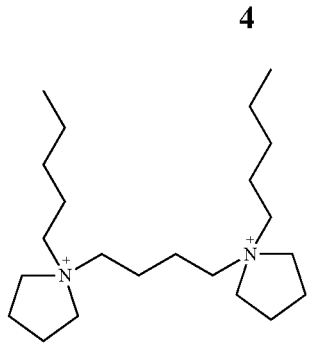

(b) 1,5-bis(N-pentylpyrrolidinium)pentane dications, which can be represented by the following formula:

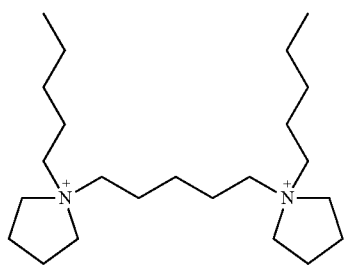

and
(c) 1,6-bis(N-pentylpyrrolidinium)hexane dications which can be represented by the following formula:

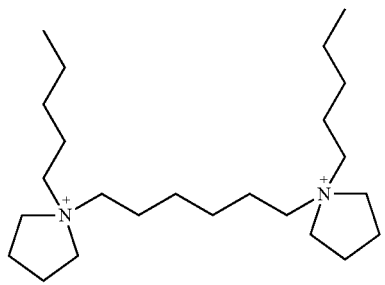

The diquaternary ammonium compounds (a), (b) and (c) can readily be synthesized by a reaction of N-pentylpyrrolidine with 1,4-dibromobutane, 1,5-dibromopentane and 1,6-dibromohexane, respectively.

The process of producing the ZSM-5 crystals includes preparing a synthesis mixture comprising sources of water, an alkali or alkaline earth metal (M), hydroxide ions, an oxide of a tetravalent element Y, such as silicon and/or germanium, optionally a trivalent element X, such as aluminum, and a structure directing agent (Q) selected from one or more of 1,4-bis(N-pentylpyrrolidinium)pentane dications, 1,5-bis(N-pentylpyrrolidinium)pentane dications, or 1,6-bis(N-pentylpyrrolidinium)hexane dications, the synthesis mixture having a composition, in terms of mole ratios of oxides, within the following ranges:

| Reactants | Useful | Preferred |
|---|---|---|
| $YO_2/X_2O_3$ | at least 20 | at least 24 |
| $H_2O/YO_2$ | 10-60 | 20-50 |

| Reactants | Useful | Preferred |
|---|---|---|
| OH$^-$/YO$_2$ | 0.2-0.6 | 0.25-0.50 |
| M/YO$_2$ | 0.05-0.40 | 0.1-0.40 |
| Q/YO$_2$ | 0.05-0.20 | 0.05-0.20 |

Suitable sources of the tetravalent element Y depend on the element Y selected but in the preferred embodiments, in which Y is silicon and/or germanium, include colloidal suspensions of silica, fumed silicas, precipitated silicas, alkali metal silicates, tetraalkyl orthosilicates and germanium oxide. If present, the trivalent element X is normally aluminum, and suitable sources of aluminum include hydrated alumina and water-soluble aluminum salts, such as aluminum nitrate. Combined sources of aluminum and silicon may include clays or treated clays such as metakaolin. Other combined sources of X and Y, including aluminosilicate zeolites, such as zeolite Y, may also be used.

Suitable sources of Q are the hydroxides and/or salts of the relevant diquaternary ammonium compounds.

In some embodiments, the synthesis mixture may also use seeds of a molecular sieve material, such as ZSM-5 from a previous synthesis, desirably in an amount from 0.01 ppm by weight to 10,000 ppm by weight, such as from 100 ppm by weight to 5,000 ppm by weight of the synthesis mixture.

Crystallization of ZSM-5 from the above synthesis mixture can be carried out at either static or stirred conditions in a suitable reactor vessel, such as for example, polypropylene jars or teflon lined or stainless steel autoclaves, at a temperature from 80° C. to 200° C., such as from 100° C. to 180° C., for a time sufficient for crystallization to occur at the temperature used, e.g., from 1 to 21 days. Thereafter, the crystals are separated from the liquid and recovered.

The product of the synthesis process is ZSM-5 having a composition comprising the molar relationship:

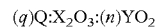
$(q)Q:X_2O_3:(n)YO_2$ wherein $0<q/n\leq0.05$, n is at least 20, and Q, X and Y have the meanings indicated above.

As taught by U.S. Pat. No. 3,702,886 and U.S. Pat. No. Re. 29,948, a typical preparation of ZSM-5 has an X-ray diffraction pattern including the characteristic lines listed in Table 1 below:

TABLE 1

| Interplanar d-Spacing (Å) | Degrees two-theta | Relative Intensity (100 × I/I$_o$) |
|---|---|---|
| 11.10 ± 0.25 | 7.98 ± 0.17 | s-vs |
| 9.85 ± 0.30 | 9.03 ± 0.28 | m-vs |
| 6.70 ± 0.10 | 13.22 ± 0.20 | w |
| 6.34 ± 0.10 | 14.06 ± 0.22 | w |
| 5.98 ± 0.10 | 14.81 ± 0.25 | w |
| 5.57 ± 0.10 | 15.91 ± 0.29 | w |
| 5.00 ± 0.10 | 17.74 ± 0.36 | w |
| 4.36 ± 0.10 | 20.38 ± 0.48 | w |
| 4.25 ± 0.08 | 20.90 ± 0.40 | w |
| 4.08 ± 0.05 | 21.79 ± 0.27 | w |
| 3.85 ± 0.07 | 23.08 ± 0.46 | m-vs |
| 3.71 ± 0.05 | 23.99 ± 0.33 | w-m |
| 3.62 ± 0.04 | 24.59 ± 0.27 | w |
| 3.04 ± 0.03 | 29.39 ± 0.30 | w |
| 2.99 ± 0.02 | 29.89 ± 0.21 | w |

The X-ray diffraction data reported herein were collected with a Panalytical X'Pert Pro diffraction system with an Xcelerator multichannel detector, equipped with a germanium solid state detector, using copper K-alpha radiation. The diffraction data were recorded by step-scanning at 0.02 degrees of two-theta, where theta is the Bragg angle, and using an effective counting time of 2 seconds for each step. The interplanar spacings, d-spacings, were calculated in Angstrom units, and the relative intensities of the lines, I/I$_o$ is the ratio of the peak intensity to that of the intensity of the strongest line, above background. The intensities are uncorrected for Lorentz and polarization effects. The relative intensities are given in terms of the symbols vs=very strong (75-100), s=strong (50-74), m=medium (25-49) and w=weak (0-24).

It is known that certain lines in the X-ray diffraction patterns of zeolites tend to broaden as the relevant dimension of the zeolite crystal decreases so that adjacent lines may begin to overlap and thereby appear as only partially resolved peaks or as unresolved broad peaks. In certain embodiments of the ZSM-5 produced by the present process, this line broadening results in there being only a single diffuse composite feature in the range from 21.5 to 26 degrees two-theta (d-spacing range from 4.13 to 3.42 Å) of the X-ray diffraction pattern. In such cases, the maximum of the composite peak near 24.0±0.30 degrees two-theta and the maximum of the composite peak near 24.4±0.30 degrees two-theta either appear as shoulders or form part of a large diffuse composite peak with a maximum near 23.2 (±0.20) degrees two-theta.

The as-synthesized ZSM-5 produced by the present process may be subjected to treatment to remove part or all of the organic directing agent Q used in its synthesis. This is conveniently effected by thermal treatment in which the as-synthesized material is heated at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. Alternatively, the organic directing agent Q can be removed by treatment with ozone (see, e.g., Parikh et al., Microporous and Mesoporous Materials, 76 (2004) 17-22). The organic-free product, especially in its metal, hydrogen and ammonium forms, is particularly useful in the catalysis of certain organic, e.g., hydrocarbon, conversion reactions.

To the extent desired and depending on the X$_2$O$_3$/YO$_2$ molar ratio of the material, any alkali or alkaline earth metal cations in the as-synthesized ZSM-5 can be replaced in accordance with techniques well known in the art by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups 2 to 15 of the Periodic Table of the Elements. As used herein, the numbering scheme for the Periodic Table Groups is as disclosed in Chemical and Engineering News, 63(5), 27 (1985).

The present molecular sieve may be intimately combined with a hydrogenating component, such as molybdenum, rhenium, nickel, cobalt, chromium, manganese, or a noble metal, such as platinum or palladium, where a hydrogenation-dehydrogenation function is to be performed. Such component can be in the composition by way of (1) cocrystallization, (2) exchanged into the composition to the extent a Group IIIA element, e.g., aluminum, is in the structure, (3) impregnated therein, or (4) intimately physically admixed therewith. Such component can be impregnated in, or on to it, such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The present molecular sieve, when employed either as an adsorbent, or as a catalyst, should be dehydrated, at least partially. This can be done by heating to a temperature in the range of 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the ZSM-5 in a vacuum, but a longer time is required to obtain a sufficient amount of dehydration.

The ZSM-5 described herein can be used as an adsorbent or, particularly in its aluminosilicate form, as a catalyst to catalyze a wide variety of organic compound conversion processes including many of present commercial/industrial importance. Examples of chemical conversion processes which are effectively catalyzed by the present ZSM-5 are those where high acid activity and large surface area are important.

As in the case of many catalysts, it may be desirable to incorporate the present ZSM-5 with another material resistant to the temperatures and other conditions employed in organic conversion processes. Such materials include active and inactive materials, and synthetic or naturally occurring zeolites, as well as, inorganic materials, such as clays, silica and/or metal oxides such as alumina. The latter may be either naturally occurring, or in the form of gelatinous precipitates, or gels including mixtures of silica and metal oxides. Use of a material in conjunction with the present ZSM-5, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the present ZSM-5 include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined, or initially subjected to calcination, acid treatment or chemical modification. Binders useful for compositing with ZSM-5 also include inorganic oxides, such as silica, zirconia, titania, magnesia, beryllia, alumina, and mixtures thereof.

In addition to the foregoing materials, the present ZSM-5 can be composited with a porous matrix material such as silica-alumina, silica-magnesia, silica-zirconia, silica-thoria, silica-beryllia, silica-titania, as well as, ternary compositions, such as silica-alumina-thoria, silica-alumina-zirconia silica-alumina-magnesia and silica-magnesia-zirconia.

The relative proportions of ZSM-5 and inorganic oxide matrix may vary widely, with the ZSM-5 content ranging from about 1 to about 90 percent by weight, and more usually, particularly when the composite is prepared in the form of beads, in the range of about 2 to about 80 weight percent of the composite.

The invention will now be more particularly described with reference to the following Examples and the accompanying drawings.

Example 1: Preparation of the C4 Diquat of N-pentylpyrrolidine

N-pentylpyrrolidine is initially prepared by the reductive amination of pentanal with pyrrolidine according to the following procedure.

500 mL tetrahydrofuran (THF) was placed in a 1-L suction flask equipped with a nitrogen gas flow. 31.9 g pentanal (0.37 mol) and then 24.9 g pyrrolidine (0.35 mol) were mixed into the THF. With the nitrogen flow turned off, 100 g of sodium triacetoxyborohydride powder was then added in 5-10 g increments to the solution. During the addition, vigorous stirring was used to ensure that the powder did not clump at the bottom of the flask and to ensure the efficient mixing of the suspension. After each addition of the sodium triacetoxyborohydride powder, adequate time was provided to form a uniform slurry before the next addition of the powder. Once all of the powder had been added, the nitrogen flow was then turned on. After two days the product was worked up by quenching the suspension with the slow addition of 275 g of a 24% potassium hydroxide (KOH) solution. The product was then extracted from the resultant solution with pentane. The organic fraction was then collected with a separatory funnel and dried with anhydrous magnesium sulfate. The amine product was then isolated by rotary evaporation of the THF and pentane solvents under reduced pressure.

The C4 diquat was formed by the reaction between N-pentylpyrrolidine and 1,4-dibromobutane. 20.0 g N-pentylpyrrolidine (0.14 mol) was added to 65 mL acetonitrile inside a 125-mL Teflon liner. 13.93 g 1,4-dibromobutane (0.064 mol) was added to the mixture. The liner was then capped, sealed inside a Parr steel autoclave, and then heated at 80° C. for 4 days. The solid precipitates were then collected by filtration and washed with acetone. After the acetone wash, additional product precipitated within the filtrate. The combined solids were then washed with ether and allowed to dry. The total yield of clean product was 18.8 g. $^1$H and $^{13}$C NMR showed the product to be pure. The dibromide salt was then ion-exchanged into the hydroxide form by dissolving it in water and passing it through a column of Dowex LC NG hydroxide exchange resin. The concentration of the aqueous solution was determined by titration with a standard solution of 0.1 N hydrochloric acid (HCl).

The C5 and C6 diquat salts of N-pentylpyrrolidine were prepared in similar fashion by using 1,5-dibromopentane and 1,6-dibromohexane, respectively, in place of the 1,4-dibromobutane.

Example 2: Synthesis of ZSM-5 with the C4 Diquat of N-pentylpyrrolidine

This synthesis was performed with a hydroxide-exchanged form of the C4 diquat of N-pentylpyrrolidine (prepared from the reaction of 1,4-dibromobutane with N-pentylpyrrolidine). 55.1 g of the diquat solution ([OH$^-$]

=1.02 mmol/g) were mixed with 49.1 g 1 N KOH and 22.4 g deionized water. 1.59 g fumed alumina was added and the mixture was thoroughly mixed to create a uniform suspension. 41.6 g Ludox AS-40 colloidal silica was then mixed into the suspension. The mixture was placed inside a Teflon liner and sealed inside a 300-mL capacity Parr autoclave with an overhead stirrer. The overhead stirrer was set at 150 rpm. The gel was heated to 160° C. over a 4-hr period. After 3 days, a sample was removed (online) from the autoclave and worked up for powder X-ray diffraction (XRD) analysis. The product was predominantly a layered phase with an intense peak around 4.5 degrees two-theta with a trace amount of the ultra-small ZSM-5. At this point, the temperature was decreased to 150° C. After an additional 22 hours at 150° C., the product was ultra-small ZSM-5 with a small amount of the layered impurity. After a further 2 hours, the product was pure ZSM-5. FIG. 1 compares the powder XRD patterns of the sequence of sampling points taken at 3 days, at 2 hours before completion, and at completion after 4 days.

Figure 2:
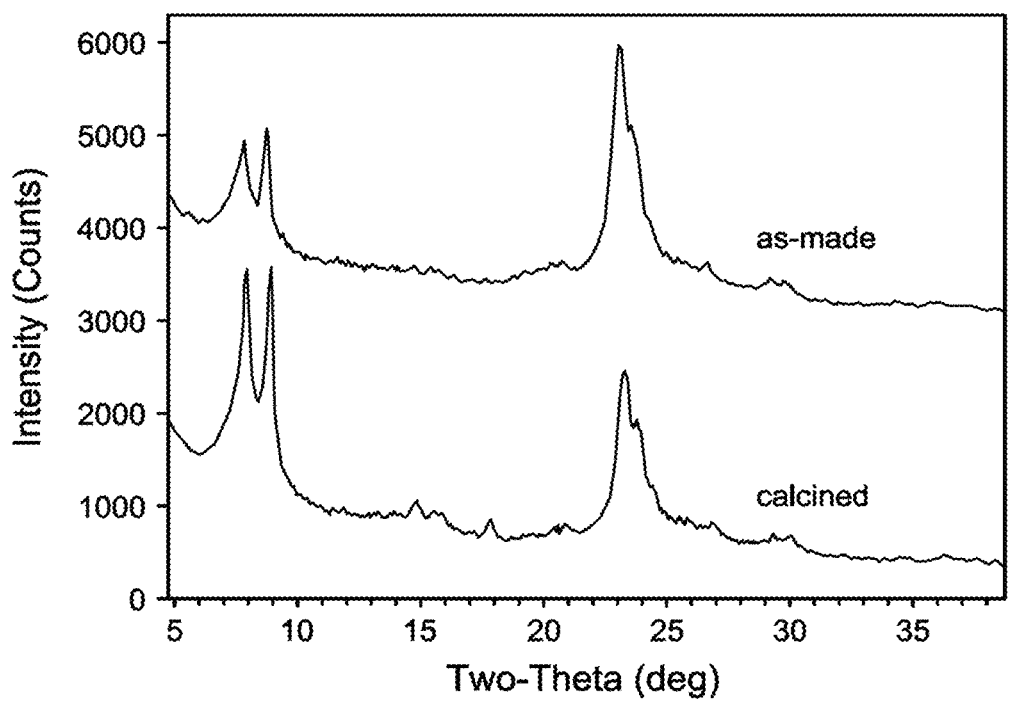
FIG. 2 compares the X-ray diffraction patterns of the product of Example 2 after crystallization for 4 days before calcination (top pattern) and after calcination (bottom pattern).

The product of the 4 day synthesis was then recovered by filtration, washed with at least 500 mL deionized water, washed with acetone, and dried in a vacuum oven at 60° C. overnight. The zeolite was then calcined in a muffle furnace by heating in a nitrogen stream from ambient temperature to 400° C. over a 2-hr period, maintaining this temperature for 15 minutes, switching the gas stream to air, increasing the temperature from 400° C. to 600° C. over a 2-hr period, maintaining the temperature at 600° C. for 2 hours, and then allowing the furnace to cool to ambient conditions. FIG. 2 compares the powder XRD patterns of the as-made and calcined products.

Figure 3:
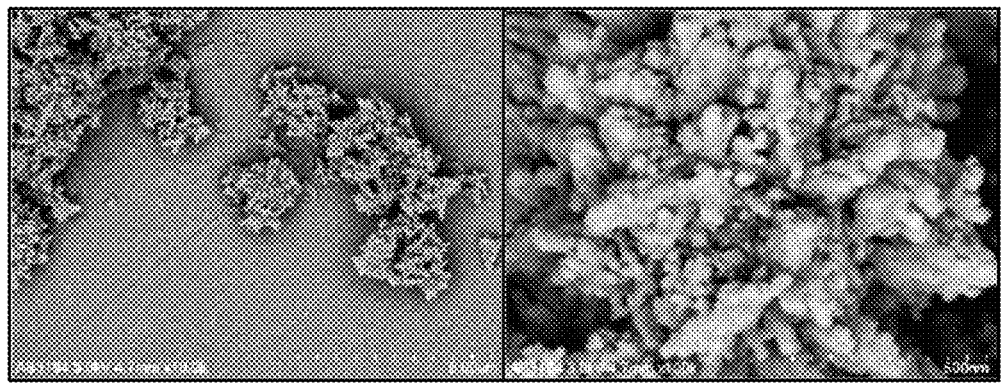
FIG. 3 provides scanning electron microscope (SEM) images of the as-synthesized product of Example 2.

Scanning electron microscope (SEM) images of the as-made product of the 4 day synthesis are shown in FIG. 3 and demonstrate the bulk material to be crystalline. Transmission electron microscopy (TEM) shows the crystals are in the form of ultra-small primary crystallites with plate-like morphologies about 20-60 nm on their edges. Microtomy of these crystals shows that the particles are less than 100 Å in thickness. The crystallites are aggregated into larger secondary particles having an average size of about 1 micron.

The calcined product of the 4 day synthesis was ion-exchanged into the ammonium form by adding 7.0 g zeolite to a solution containing an equal mass of ammonium nitrate (7.0 g) and a 10-fold mass of deionized water (70 g). The slurry was placed in a polypropylene bottle and heated within a steambox overnight at 98° C. The zeolite was then filtered and washed with at least 300 mL deionized water. The zeolite was converted to the acidic form by calcining the zeolite from ambient conditions to 500° C. over a 2-hour period, maintaining that temperature for 4 hours, and then allowing the furnace to cool to near-ambient conditions. Analysis of nitrogen physisorption data by the t-plot method showed that the preparation had 124 $m^2/g$ external surface area and 0.13 cc/g micropore volume (318 $m^2/g$ internal surface area).

Example 3: Synthesis of ZSM-5 with the C5 Diquat of N-pentylpyrrolidine

Figure 4:
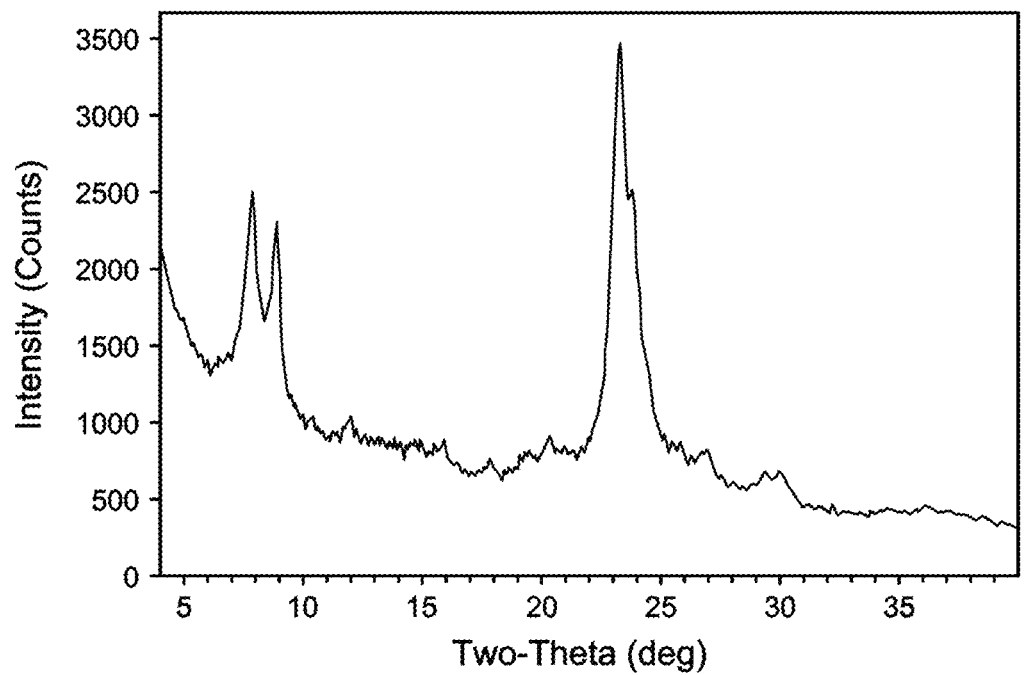
FIG. 4 shows the X-ray diffraction pattern of the as-synthesized product of Example 3.

This synthesis was performed with a hydroxide-exchanged form of the C5 diquat of N-pentylpyrrolidine (prepared from the reaction of 1,5-dibromobutane with N-pentylpyrrolidine). 87.2 g of the diquat solution ([OH$^-$]=0.58 mmol/g) were mixed with 44.03 g 1 N KOH. 1.05 g fumed alumina was added and the mixture was thoroughly mixed to create a uniform suspension. 37.7 g Ludox AS-40 colloidal silica was then mixed into the suspension. The mixture was placed inside a Teflon liner and sealed inside a 300-mL capacity Parr autoclave with an overhead stirrer. The overhead stirrer was set at 150 rpm. The gel was heated to 160° C. over a 4-hr period. After 24 hours a sample was removed (online) from the autoclave and worked up for powder XRD analysis. The product was pure (by XRD) ultra-small ZSM-5. FIG. 4 shows the powder XRD of the product.

Figure 5:
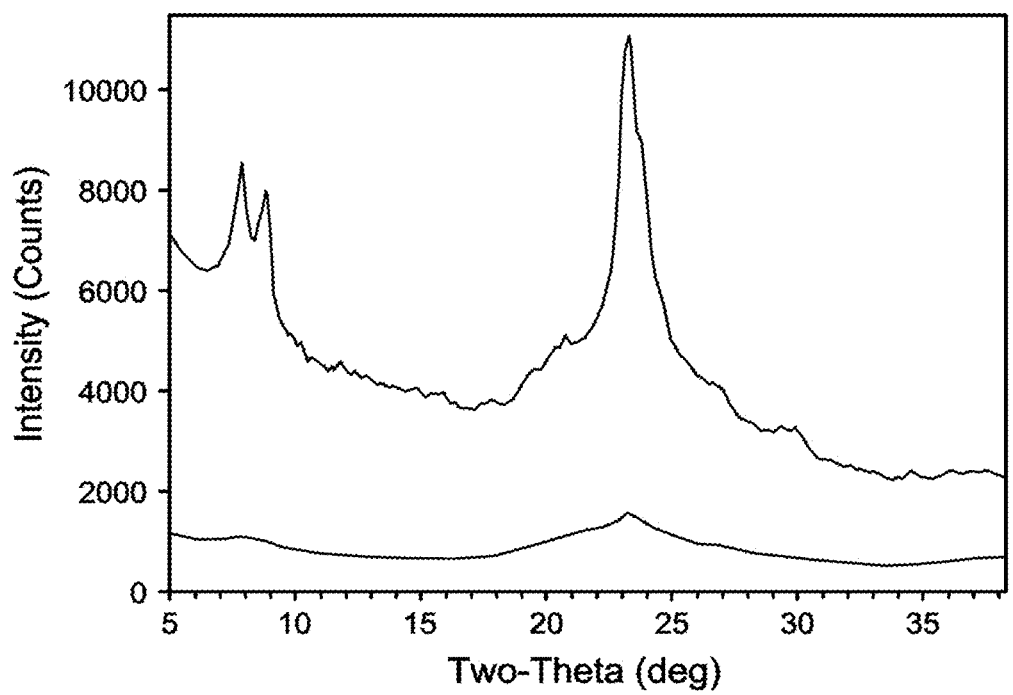
FIG. 5 compares the X-ray diffraction patterns of the as-synthesized product of Example 4 after crystallization for 24 hours (bottom pattern) and 30 hours (top pattern).

Example 4: Synthesis of ZSM-5 with the C5 Diquat of N-pentylpyrrolidine 5.21 g of the diquat solution used in Example 3 ([OH$^-$]=0.58 mmol/g) were mixed with 2.63 g 1 N KOH. 0.063 g SpectrAl fumed alumina (Cabot) was added and the mixture was thoroughly mixed to create a uniform suspension. 2.25 g Ludox AS-40 colloidal silica was then mixed into the suspension. The mixture was placed inside a Teflon liner and sealed inside a 23-mL capacity Parr autoclave. The autoclave was placed inside an oven at 150° C. with a rotisserie and tumbled at 50 rpm. The gel was heated for 24 hours and then removed and sampled. The autoclave was then placed back in an oven and heated an additional 6 hours. The product after 30 total hours of heating was ultra-small ZSM-5 with some remaining amorphous material. FIG. 5 shows the powder XRD of the products.

Example 5: Synthesis of ZSM-5 with the C5 Diquat of N-pentylpyrrolidine

Figure 6:
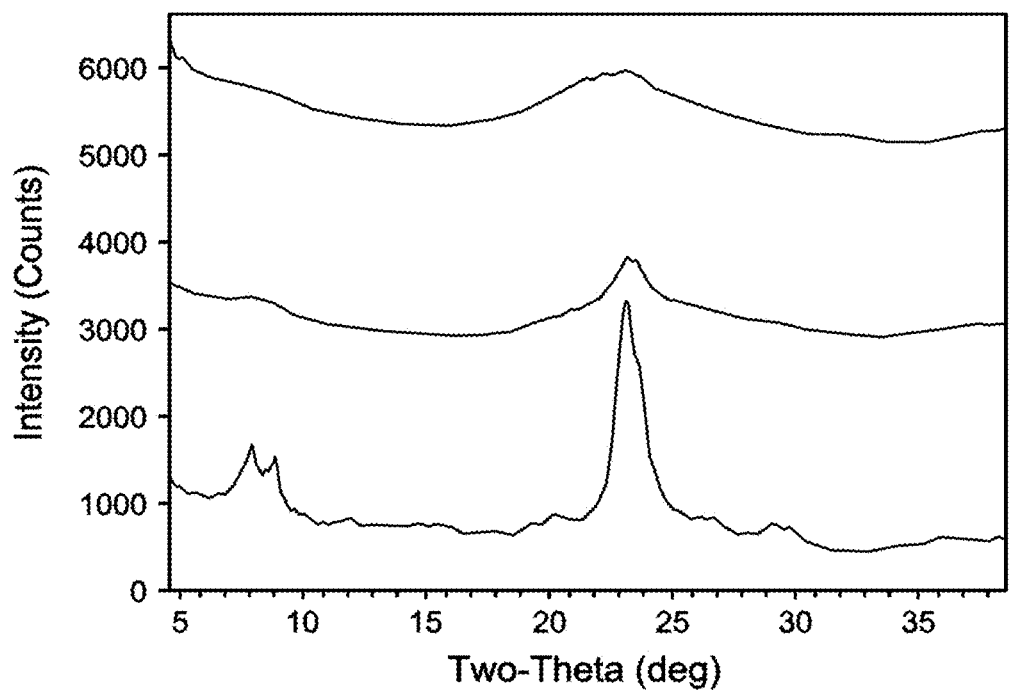
FIG. 6 compares the X-ray diffraction patterns of the as-synthesized product of Example 5 after crystallization for 1 day (top pattern), 2 days (middle pattern) and 6 days (bottom pattern).

Example 3 was repeated except the synthesis temperature was maintained at 130° C. After 24 hours, the reaction was sampled and the product was amorphous by XRD. After 2 days, the product was still mostly amorphous, but some ZSM-5 appeared. The reaction was then sampled again after 6 total days of heating. The XRD of the product showed it to be pure ultra-small ZSM-5. FIG. 6 shows the powder XRD for the samples taken after 1, 2 and 6 days of heating.

Example 6: Synthesis of ZSM-5 with the C5 Diquat of N-pentylpyrrolidine

Figure 7:
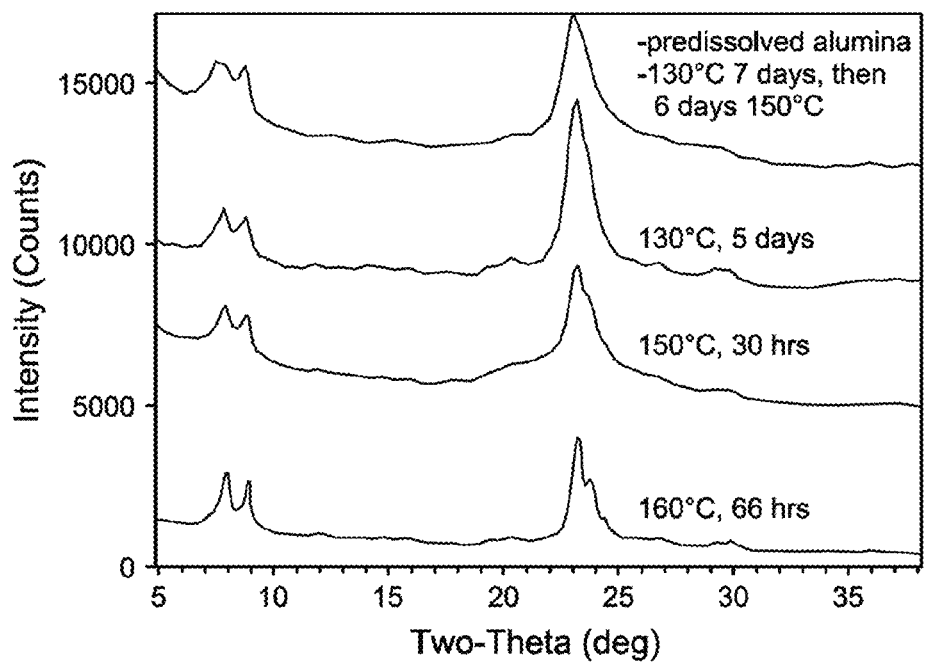
FIG. 7 compares the X-ray diffraction patterns of the as-synthesized products of Example 6.

Four further repeat experiments of the process of Example 3 were conducted. In the first experiment crystallization was carried out at 160° C. for 66 hours, whereas in the second and third experiments crystallization was carried out at 150° C. for 30 hours and 130° C. for 5 days, respectively. In the fourth experiment, fumed alumina was pre-dissolved in the KOH/diquat solution by heating the mixture at 160° C. for about 45 minutes before adding the silica. Crystallization was then conducted by heating at 130° C. for 7 days followed by heating at 150° C. for 6 days. The results are shown in FIG. 7 and demonstrate that reducing the temperature resulted in products having significantly decreased crystal size as inferred from the peak broadening in the powder XRD patterns.

Figure 8:
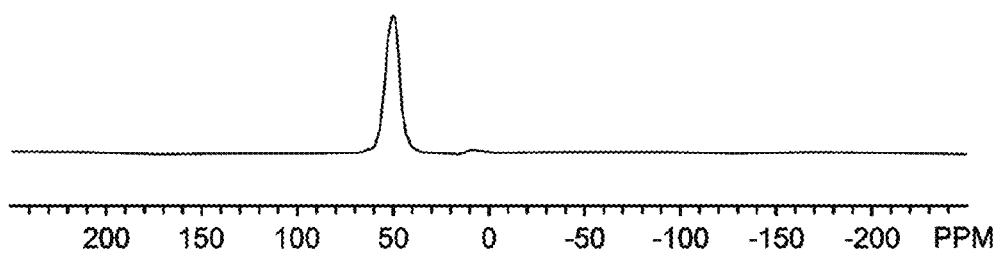
FIG. 8 shows the $^{27}$Al MAS NMR of the product of the fourth experiment of Example 6 prepared with pre-dissolved fumed alumina FIG. 9 provides SEM images of the product of the fourth experiment of Example 6.

The product of the fourth experiment was calcined as in Example 1 and was subjected to nitrogen physisorption measurements. Analysis of the data by the t-plot method showed the product to possess 247 $m^2/g$ internal surface area (0.107 cc/g micropore volume) and 370 $m^2/g$ external surface area. $^{27}$Al MAS NMR spectrum of the product of the fourth experiment is given in FIG. 8 and shows that the calcined product has >95% tetrahedral aluminum. In contrast, the product obtained from the synthesis without predissolution of the fumed alumina (see Example 4) contains only about 10% tetrahedral aluminum.

Figure 9:
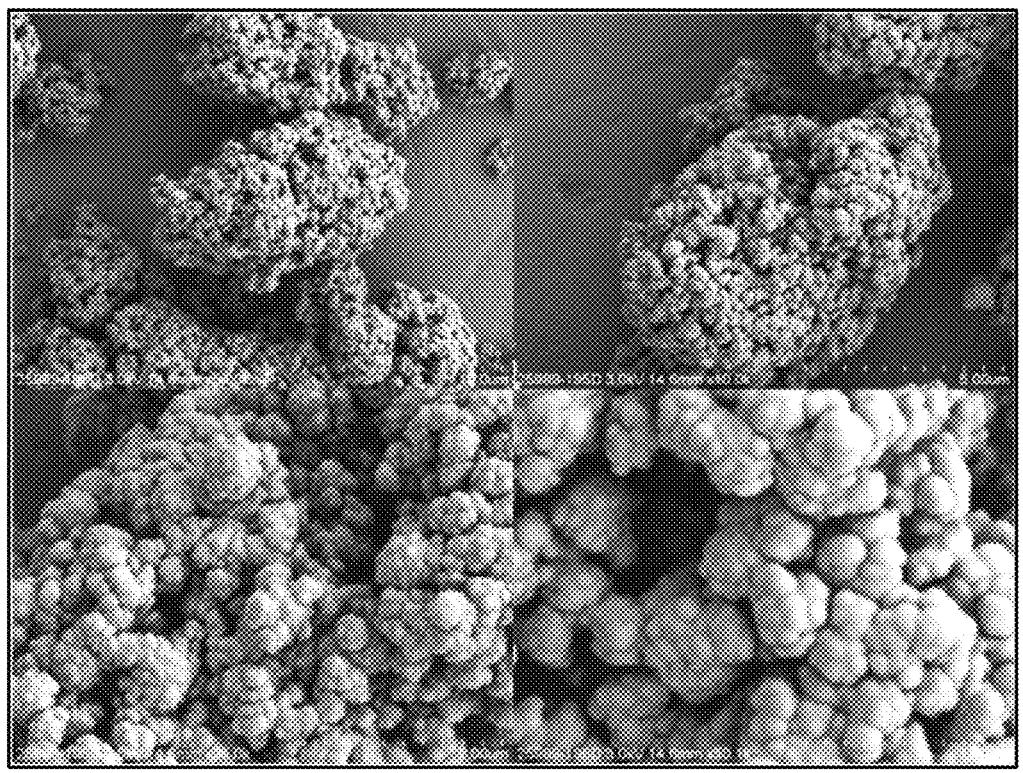
Figure 10A:
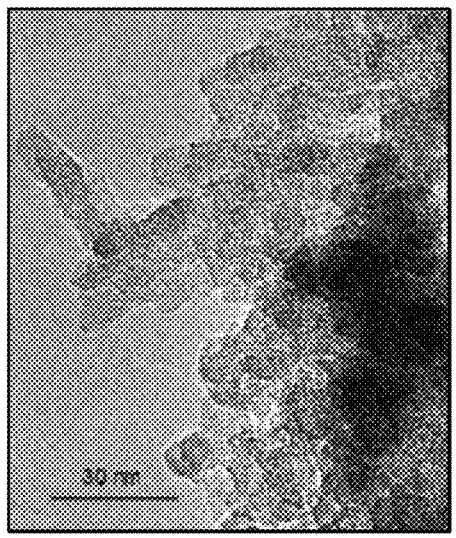
FIG. 10 shows transmission electron micrograph (TEM) images of a microtomed specimen of a sample of the fourth experiment product of Example 6.
Figure 10B:
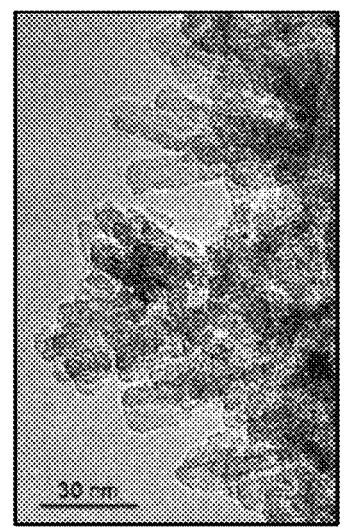
Figure 10C:
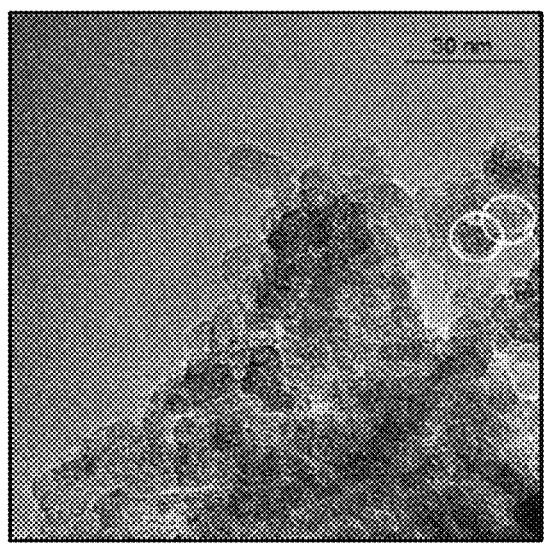

SEM images of the product of the fourth experiment are shown in FIG. 9. The TEM images in FIGS. 10(a) and 10(b) demonstrate that many of the crystals are elongated with lengths that are generally less than 30 nm and widths that are less than 10 nm. Other TEM images (FIG. 10(c)) show more isotropically shaped crystals with shorter lengths (10-20 nm) than those in FIGS. 10(a) and 10(b). The mean and median crystal lengths were 15 and 14 nm, respectively and the mean and median widths were 8.2 and 8.0 nm, respectively.

Figure 10D:
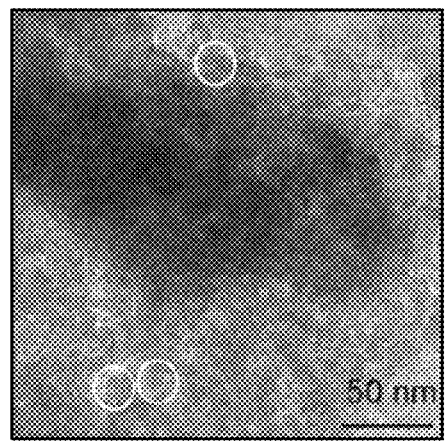
Figure 11:
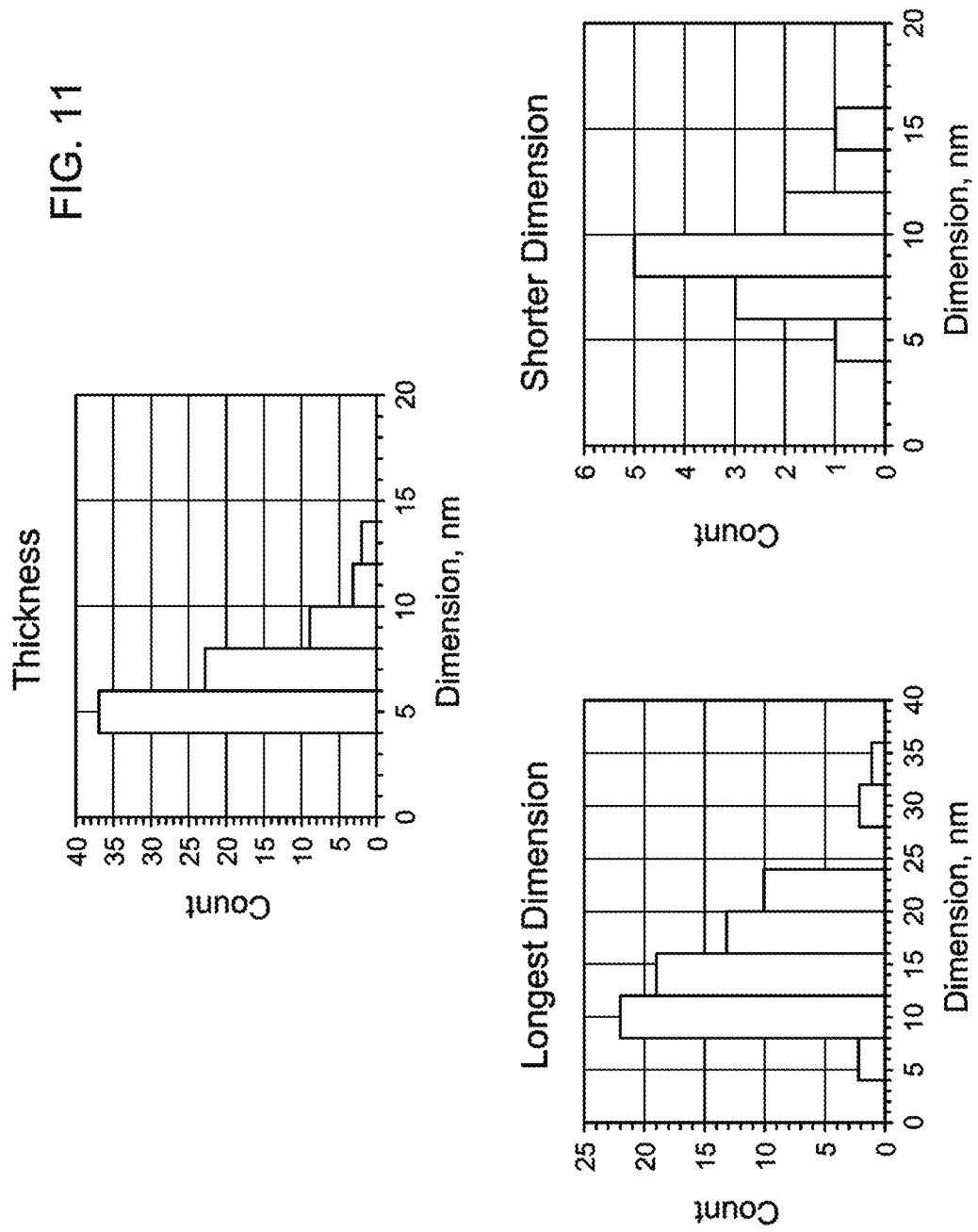
FIG. 11 is a bar graph showing the distribution of crystal dimensions for each of the crystallographic edges of a sample of the fourth experiment product of Example 6.

FIG. 10(d) shows a TEM image of a microtomed specimen of a sample of fourth experiment product. The images of the microtomed crystals reveal the thickness of the crystals; the crystal dimensions here are mostly 5-7 nm. The mean and median thicknesses were 6.4 and 6.0 nm, respectively. The bar graphs in FIG. 11 show the distribution of crystal dimensions for each of the crystallographic edges.

Example 7: Synthesis of ZSM-5 with the C5 Diquat of N-pentylpyrrolidine

Figure 12:
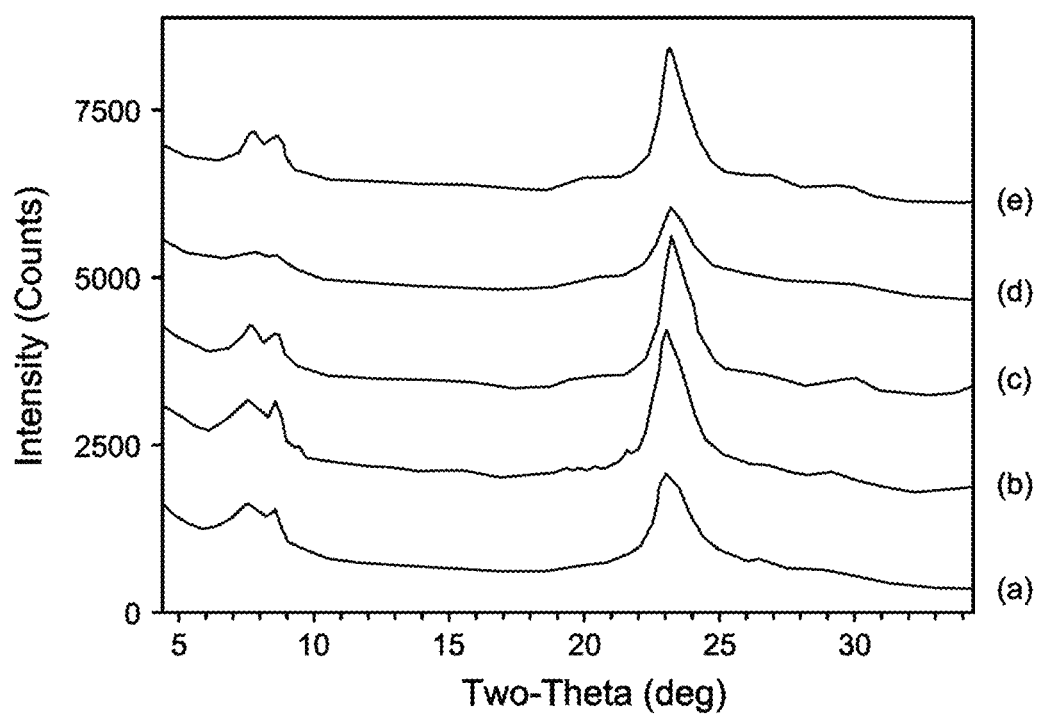
FIGS. 12 (a) to (e) show the X-ray diffraction patterns of the as-synthesized products of Examples 7 to 11, respectively.

A solution was prepared by mixing 5.21 g of a hydroxide solution of the C5 diquat of N-pentylpyrrolidine ([OH]=0.58 mmol/g) with 2.63 g 1 N KOH inside a Teflon liner for a 23-mL steel Parr autoclave. 0.063 g SpectrAl fumed alumina (Cabot) was mixed into the solution to create a uniform suspension. The liner was then capped, sealed inside the 23 mL autoclave, and heated at 160° C. under tumbling conditions (~50 rpm) inside a convection oven for about 45 minutes in order to dissolve most of the alumina. The reactor was then cooled and 2.25 g Ludox AS-40 was then mixed into the suspension. The liner was then capped, sealed inside the 23-mL autoclave, and heated at 160° C. under tumbling conditions (~50 rpm) inside a convection oven for 8 days. The solids were then isolated by filtering through a Buchner funnel, washing with deionized water, and drying in an oven at 100° C. FIG. 12(a) shows the powder XRD of the product.

Example 8: Synthesis of ZSM-5 with the C5 Diquat of N-pentylpyrrolidine

The process of Example 7 was repeated except that 0.04 g of seeds from that preparation were added and the gel was heated for a total of 6 days instead of 8. The powder XRD shown in FIG. 12(b) is consistent with the product being ultra-small ZSM-5 with a trace level of MCM-68.

Example 9: Synthesis of ZSM-5 with the C6 Diquat of N-pentylpyrrolidine

A solution was prepared by mixing 3.51 g of a hydroxide solution of the C6 diquat of N-pentylpyrrolidine ([OH]=0.86 mmol/g) with 2.63 g 1 N KOH inside a Teflon liner for a 23-mL steel Parr autoclave. 0.063 g SpectrAl fumed alumina (Cabot) was mixed into the solution to create a uniform suspension. The liner was then capped, sealed inside the 23 mL autoclave, and heated at 160° C. under tumbling conditions (~50 rpm) inside a convection oven for about 45 minutes in order to dissolve most of the alumina. The reactor was then cooled and 2.25 g Ludox AS-40 was then mixed into the suspension. The liner was then capped, sealed inside the 23-mL autoclave, and heated at 125° C. under tumbling conditions (~50 rpm) inside a convection oven for 9 days. The solids were then isolated by filtering through a Buchner funnel, washing with deionized water, and drying in an oven at 100° C. FIG. 12(c) (c) shows the powder XRD of the product.

The zeolite was heated inside a muffle furnace from ambient temperature to 400° C. at 4° C./min under a nitrogen atmosphere, then heated to 600° C. at 4° C./min in air, and maintained at 600° C. in air for 2 hours. After the sample cooled to ambient temperature, it was ammonium-exchanged by adding the zeolite to a 10-fold mass of water and adding an equivalent mass of ammonium nitrate. The ammonium-exchange was carried out overnight in a steam box at a temperature of 98-99° C. The zeolite was then filtered and washed exhaustively with deionized water to remove excess salt. The zeolite was then calcined to 500° C. to obtain the fully acidic form of the zeolite. Analysis by the t-plot method of nitrogen physisorption shows the sample possesses 222 m$^2$/g external surface area and 0.14 cc/g micropore volume (326 m$^2$/g internal surface area).

Example 10: Synthesis of ZSM-5 with the C6 Diquat of N-pentylpyrrolidine

A solution was prepared by mixing 3.51 g of a hydroxide solution of the C6 diquat of N-pentylpyrrolidine ([OH] 0.86 mmol/g) with 0.15 g 50% KOH inside a Teflon liner for a 23-mL steel Parr autoclave. 0.063 g SpectrAl fumed alumina (Cabot) was mixed into the solution to create a uniform suspension. The liner was then capped, sealed inside the 23-mL autoclave, and heated at 160° C. under tumbling conditions (~50 rpm) inside a convection oven for about 45 minutes in order to dissolve most of the alumina. The reactor was then cooled and 2.25 g Ludox AS-40 was then mixed into the suspension. 0.04 g seeds from Example 7 were added. The liner was then capped, sealed inside the 23-mL autoclave, and heated at 125° C. under tumbling conditions (~50 rpm) inside a convection oven for 14 days and then at 140° C. for an additional 4 days. The solids were then isolated by filtering through a Buchner funnel, washing with deionized water, and drying in an oven at 100° C. The powder XRD of the product is shown in FIG. 12(d).

Example 11: Synthesis of ZSM-5 with the C6 Diquat of N-pentylpyrrolidine

A solution was prepared by mixing 3.51 g of a hydroxide solution of the C6 diquat of N-pentylpyrrolidine ([OH]=0.86 mmol/g) with 2.63 g 1 N KOH inside a Teflon liner for a 23-mL steel Parr autoclave. 0.097 Alcoa-C31 alumina trihydrate was mixed into the solution to create a uniform suspension. The liner was then capped, sealed inside the 23-mL autoclave, and heated at 160° C. under tumbling conditions (~50 rpm) inside a convection oven for about 45 minutes in order to dissolve the alumina, The reactor was then cooled and 2.25 g Ludox AS-40 was then mixed into the suspension. The liner was then capped, sealed inside the 23-mL autoclave, and heated at 140° C. under tumbling conditions (~50 rpm) inside a convection oven for 7 days. The solids were then isolated by filtering through a Buchner funnel, washing with deionized water, and drying in an oven at 100° C. The powder XRD of the product is shown in FIG. 12(e).

Figure 13:
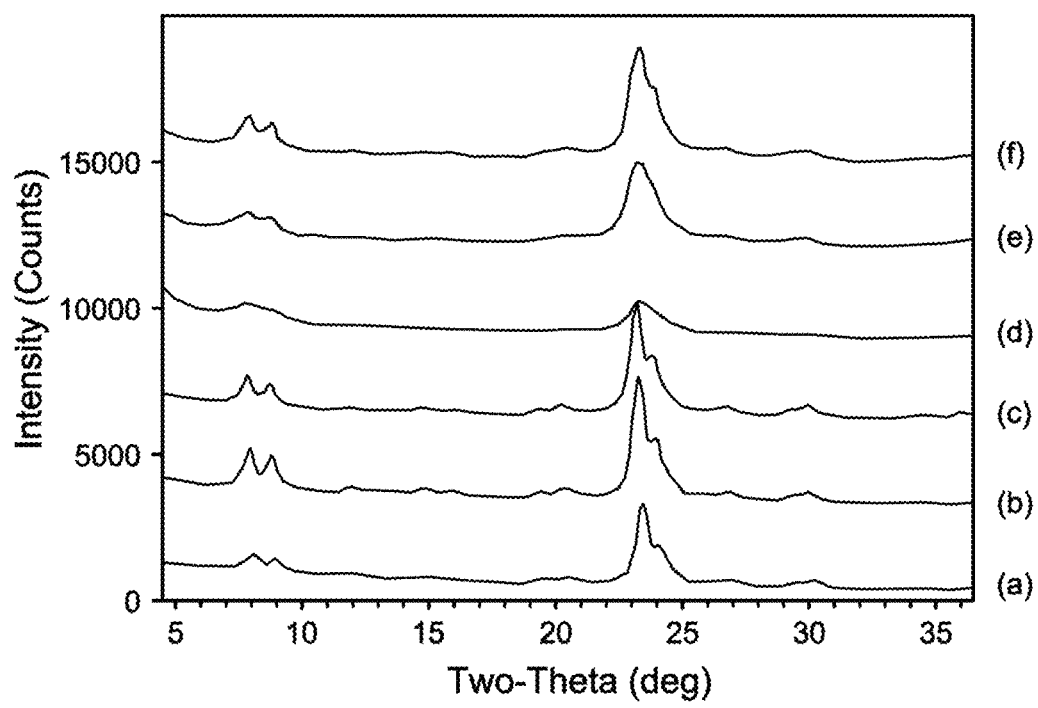
FIGS. 13 (a) to (f) show the X-ray diffraction patterns of the as-synthesized products of Examples 12 to 17, respectively.

Example 12: Synthesis of Borosilicate ZSM-5 with the C6 Diquat of N-pentylpyrrolidine A solution was prepared by mixing 3.51 g of a hydroxide solution of the C6 diquat of N-pentylpyrrolidine ([OH] 0.86 mmol/g) with 2.63 g of 1N KOH inside a Teflon liner for a 23-mL steel Parr autoclave. 0.046 g boric acid was then dissolved in the hydroxide solution. 2.25 g Ludox AS-40 was then added and mixed to create a uniform suspension. The liner was then capped, sealed inside the 23-mL autoclave, and heated at 100° C. under static conditions inside a convection oven for 9 days. The solids were then recovered by filtering through a Buchner funnel, washing with deionized water, and drying in an oven at 100° C. The powder XRD of the product is shown in FIG. 13(a).

Example 13: Synthesis of Borosilicate ZSM-5 with the C6 Diquat of N-pentylpyrrolidine The process of Example 12 was repeated at 125° C. under tumbling conditions (50 rpm) for 6 days. FIG. 13(b) shows the powder XRD of the product.

Example 14: Synthesis of all Silica ZSM-5 with the C6 Diquat of N-pentylpyrrolidine A solution was prepared by mixing 3.51 g of a hydroxide solution of the C6 diquat of N-pentylpyrrolidine ([OH]=0.86 mmol/g) with 2.63 g 1 N KOH inside a Teflon liner for a 23-mL steel Parr autoclave. 2.25 g Ludox AS-40 was then mixed into the suspension. The liner was then capped, sealed inside the 23-mL autoclave, and heated at 100° C. under static conditions inside a convection oven for 4 days. The solids were then isolated by centrifugation and washing three times, and drying in an oven at 100° C. The powder XRD of the product is shown in FIG. 13(c).

Example 15: Synthesis of all Silica ZSM-5 with the C5 Diquat of N-pentylpyrrolidine A solution was prepared by mixing 4.92 g of a hydroxide solution of the C5 diquat of N-pentylpyrrolidine ([OH]=0.61 mmol/g) with 2.63 g 1 N KOH inside a Teflon liner for a 23-mL steel Parr autoclave. 2.25 g Ludox AS-40 was then mixed into the suspension. The liner was then capped, sealed inside the 23-mL autoclave, and heated at 100° C. under static conditions inside a convection oven for 5 days. The solids were then isolated by centrifugation and washing three times, and drying in an oven at 100° C. The powder XRD of the product is shown in FIG. 13(d).

Example 16: Synthesis of BZSM-5 with the C5 Diquat of N-pentylpyrrolidine

A solution was prepared by mixing 4.92 g of a hydroxide solution of the C5 diquat of N-pentylpyrrolidine ([OH]=0.61 mmol/g) with 2.63 g 1 N KOH inside a Teflon liner for a 23-mL steel Paar autoclave. 0.046 g boric acid was then dissolved in the hydroxide solution. 2.25 g Ludox AS-40 was then mixed into the suspension. The liner was then capped, sealed inside the 23-mL autoclave, and heated at 125° C. under tumbling conditions (50 rpm) inside a convection oven for 13 days. The solids were then isolated by filtering through a Buchner funnel, washing with deionized water, and drying in an oven at 100° C. The powder XRD of the product is shown in FIG. 13(e).

Example 17: Synthesis of BZSM-5 with the C5 Diquat of N-pentylpyrrolidine

The process of Example 16 was repeated but the reaction mixture was heated at 140° C. for 11 days. FIG. 13(f) shows the powder XRD pattern of the product.

Example 18: Synthesis of ZSM-5 with the C5 Diquat of N-pentylpyrrolidine

A solution was prepared by mixing 4.93 g of a hydroxide solution of the C5 diquat of N-pentylpyrrolidine ([OH]=0.61 mmol/g) with 2.63 g 1 N KOH inside a Teflon liner for a 23-mL steel Parr autoclave. 0.063 g SpectrAl fumed alumina (Cabot) was mixed into the solution to create a uniform suspension. The liner was then capped, sealed inside the 23-mL autoclave, and heated at 160° C. under tumbling conditions (~50 rpm) inside a convection oven for about 45 minutes in order to dissolve most of the alumina. The reactor was then cooled and 2.25 g Ludox AS-40 was then mixed into the suspension. 0.04 g seeds from Example 7 were then added. The liner was then capped, sealed inside the 23-mL autoclave, and heated at 175° C. under tumbling conditions (~50 rpm) inside a convection oven for 3 days. The solids were then isolated by filtering through a Buchner funnel, washing with deionized water, and drying in an oven at 100° C. Powder XRD showed the product to be a mixture of ZSM-5 and MCM-68.

Example 19: Synthesis of ZSM-5 with the C5 Diquat of N-pentylpyrrolidine

Figure 14:
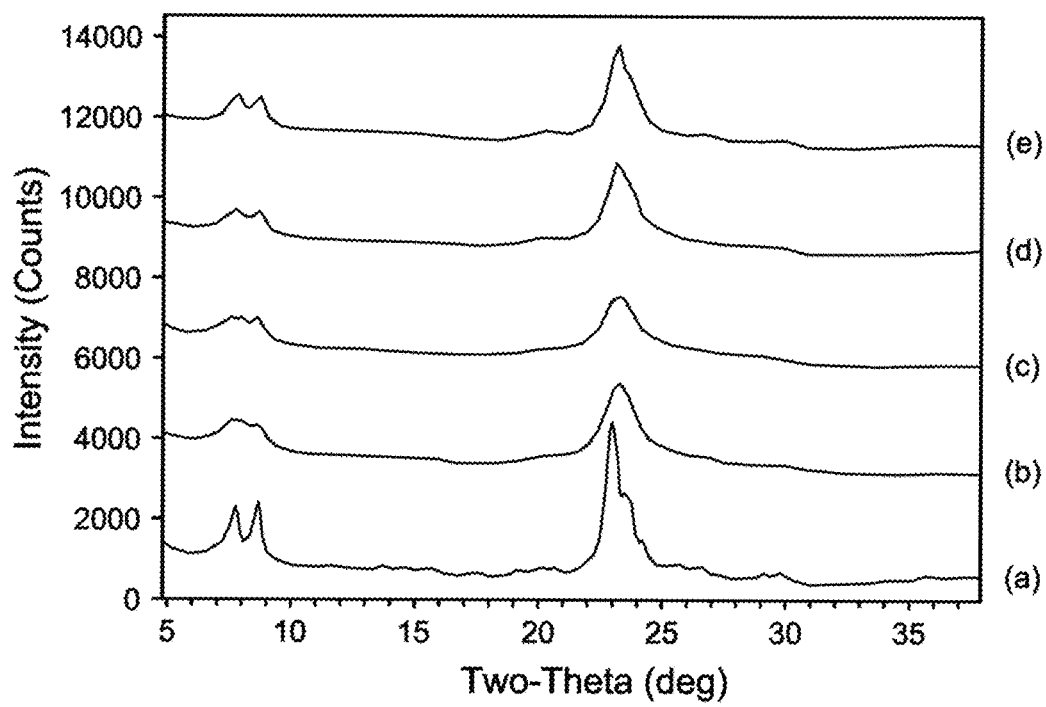
FIGS. 14 (a) to (e) show the X-ray diffraction patterns of the as-synthesized products of Examples 19 to 23, respectively.

The process of Example 18 was repeated except only 0.032 g fumed alumina was added and the reaction mixture was heated at 160° C. under tumbling conditions (~50 rpm) inside a convection oven for 9 days. FIG. 14(a) shows the powder XRD of the product.

Example 20: Synthesis of ZSM-5 with the C5 Diquat of N-pentylpyrrolidine

A solution was prepared by mixing 3.95 g of a hydroxide solution of the C5 diquat of N-pentylpyrrolidine ([OH]=0.76 mmol/g) with 2.63 g 1 N KOH and 0.88 g deionized water inside a Teflon liner for a 23-mL steel Parr autoclave. 0.015 g SpectrAl fumed alumina (Cabot) was mixed into the solution to create a uniform suspension. The liner was then capped, sealed inside the 23-mL autoclave, and heated at 160° C. under tumbling conditions (~50 rpm) inside a convection oven for about 45 minutes in order to dissolve most of the alumina. The reactor was then cooled and 2.12 g Ludox AS-40 was then mixed into the suspension. The liner was then capped, sealed inside the 23-mL autoclave, and heated at 110° C. under tumbling conditions (~50 rpm) inside a convection oven for 11 days. The solids were then isolated by filtering through a Buchner funnel, washing with deionized water, and drying in an oven at 100° C. The powder XRD pattern in FIG. 14(b) is consistent with the product being pure ultra-small ZSM-5.

Example 21: Synthesis of ZSM-5 with the C5 Diquat of N-pentylpyrrolidine

A solution was prepared by mixing 35.96 g of a hydroxide solution of the C5 diquat of N-pentylpyrrolidine ([OH]=0.76 mmol/g) with 23.91 g 1 N KOH and 11.4 g deionized water inside a Teflon liner for a 125-mL steel Parr autoclave. 0.57 g SpectrAl fumed alumina (Cabot) was mixed into the solution to create a uniform suspension. The liner was then capped, sealed inside the 125-mL autoclave, and heated at 160° C. under tumbling conditions (~50 rpm) inside a convection oven for about 45 minutes in order to dissolve most of the alumina. The reactor was then cooled and 20.45 g Ludox AS-40 was then mixed into the suspension. The liner was then capped, sealed inside the 125-mL autoclave, and heated at 150° C. under tumbling conditions (~50 rpm) inside a convection oven for 7 days. The solids were then isolated by filtering through a Buchner funnel, washing exhaustively with deionized water (about 1 liter), and drying in an oven at 100° C. The powder XRD pattern in FIG. 14(c) is consistent with the product being ultra-small ZSM-5.

Example 22: Synthesis of ZSM-5 with the C5 Diquat of N-pentylpyrrolidine

Figure 15:
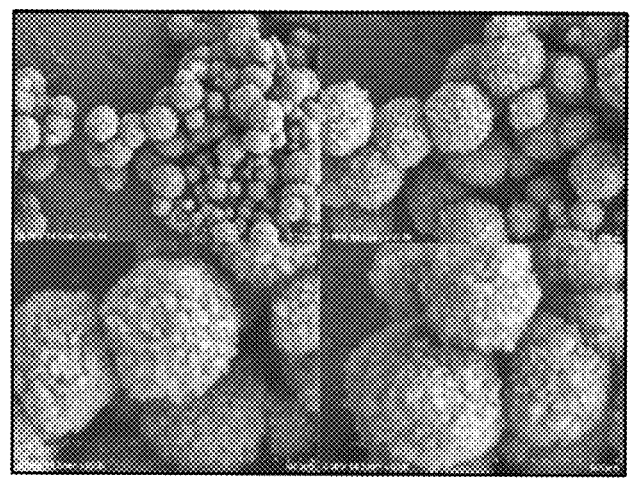
FIG. 15 provides scanning electron microscope (SEM) images of the as-synthesized product of Example 22.
Figure 16:
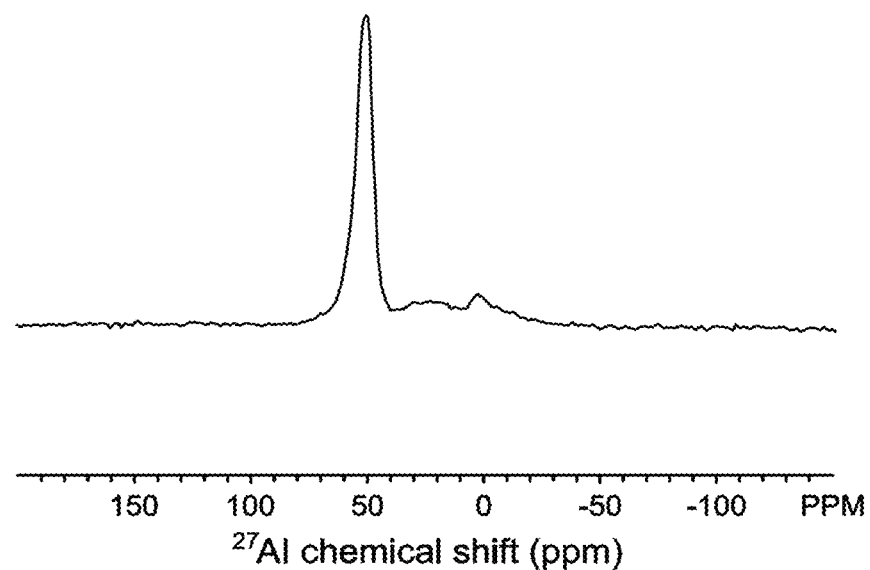
FIG. 16 shows the $^{27}$Al MAS NMR of the product of Example 22.
Figure 17:
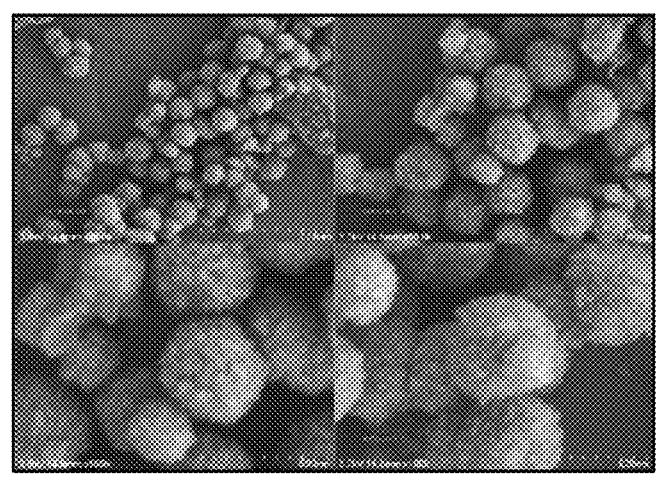
FIG. 17 shows SEM images of the product of Example 23.

A solution was prepared by mixing 3.95 g of a hydroxide solution of the C5 diquat of N-pentylpyrrolidine ([OH]=0.76 mmol/g) with 2.63 g 1 N KOH and 0.90 g deionized water inside a Teflon liner for a 23-mL steel Parr autoclave. 2.08 g Ludox AS-40 and 0.13 g metakaolin (Nusheen) were then mixed with the solution. The liner was then capped, sealed inside the 23-mL autoclave, and heated at 140° C. under tumbling conditions (~50 rpm) inside a convection oven for 3 days. The solids were then isolated by filtering through a Buchner funnel, washing with deionized water, and drying in an oven at 100° C. The powder XRD pattern in FIG. 14(d) is consistent with the product being ZSM-5 with a trace level of anatase impurity from the metakaolin reactant (peak at ~25.2 degrees two-theta). SEM images of the product are shown in FIG. 15. The product is composed of spheroidal polycrystalline aggregates that are less than 1 micron in size. The size of the individual crystallites cannot be resolved within the resolution of the SEM images. In the lowest magnification image, a few flakes can be observed that are due to some unreacted metakaolin. The presence of unreacted metakaolin is verified by $^{27}$Al MAS NMR (FIG. 16), which shows about 27% of the aluminum of the as-made product is non-tetrahedral.

Example 23: Synthesis of ZSM-5 with the C5 Diquat of N-pentylpyrrolidine

Figure 18:
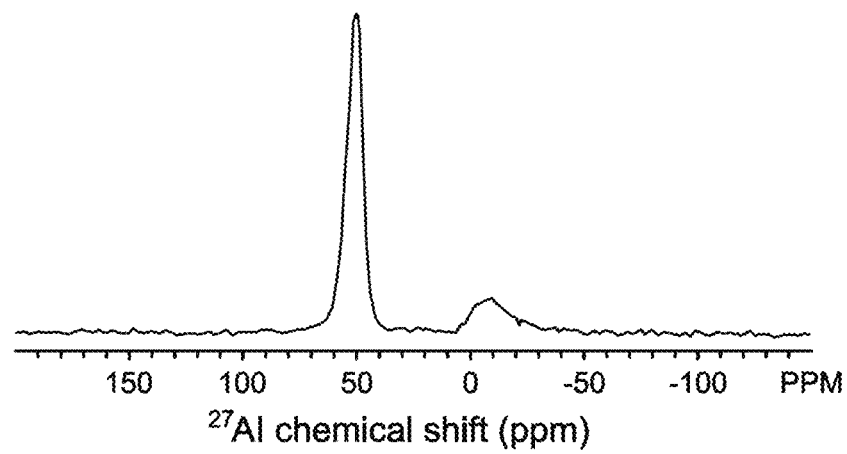
FIG. 18 shows the $^{27}$Al MAS NMR of the product of Example 23.

The process of Example 22 was repeated except that only 0.065 g metakaolin was used and the reaction was carried out at 130° C. for 3 days. The powder XRD of the product in FIG. 14(e) is somewhat sharper than that of the product from Example 22. FIG. 27 shows SEM images of the product. $^{27}$Al NMR of the product (FIG. 18) shows that 76% of the aluminum from the metakaolin reactant is incorporated into the product as tetrahedral aluminum.

Example 24: Synthesis of ZSM-5 with the C5 Diquat of N-pentylpyrrolidine

Figure 19:
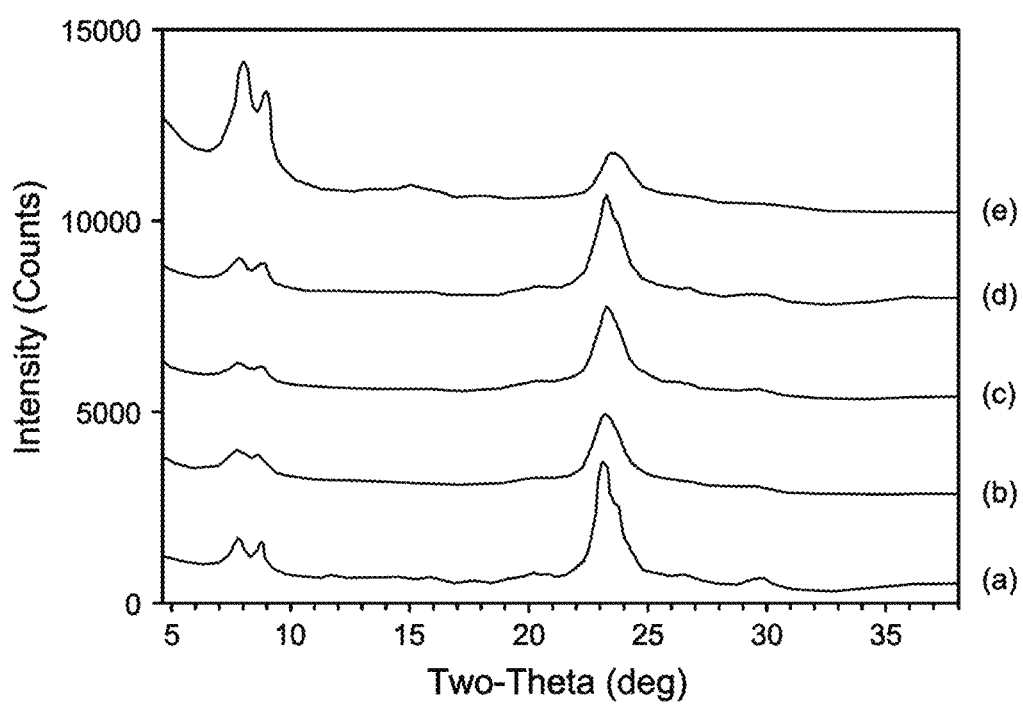
FIG. 19 (a) to (c) show the X-ray diffraction pattern of the as-synthesized product of Examples 24 to 26 and FIGS. 20 (d) and (e) show the X-ray diffraction pattern of the as-synthesized and as-calcined products of Example 27.
Figure 20:
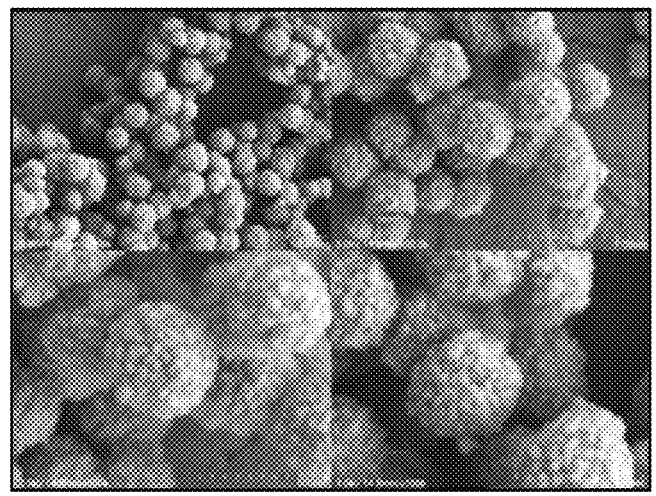
FIG. 20 shows SEM images of the product of Example 24.

The process of Example 22 was again repeated except that only 0.033 g metakaolin was used and the reaction was carried out at 130° C. for 3 days. The peaks of the powder XRD of the product [FIG. 19(a)] are somewhat sharper than those of the product from Example 22. SEM images of the product are shown in FIG. 20.

Example 25: Synthesis of ZSM-5 with the C5 Diquat of N-pentylpyrrolidine

The process of Example 22 was again repeated except that the reaction was carried out at 130° C. for 4 days. The powder XRD of the product is shown in FIG. 19(b).

Example 26: Synthesis of ZSM-5 with the C5 Diquat of N-pentylpyrrolidine

The process of Example 23 was repeated except the reaction was carried out at 120° C. for 3 days. The powder XRD of the product [FIG. 19(c)] is broader than the one for the product of Example 23.

Example 27: Synthesis of ZSM-5 with the C5 Diquat of N-pentylpyrrolidine

The process of Example 24 was repeated except the reaction was carried out at 120° C. for 3 days. The powder XRD of the product [FIG. 19(d)] is broader than the one for the product of Example 24. The product was calcined as described in Example 9. FIG. 19(e) shows the powder XRD pattern of the calcined material.

Example 28: Synthesis of ZSM-5 with the C5 Diquat of N-pentylpyrrolidine

Figure 21:
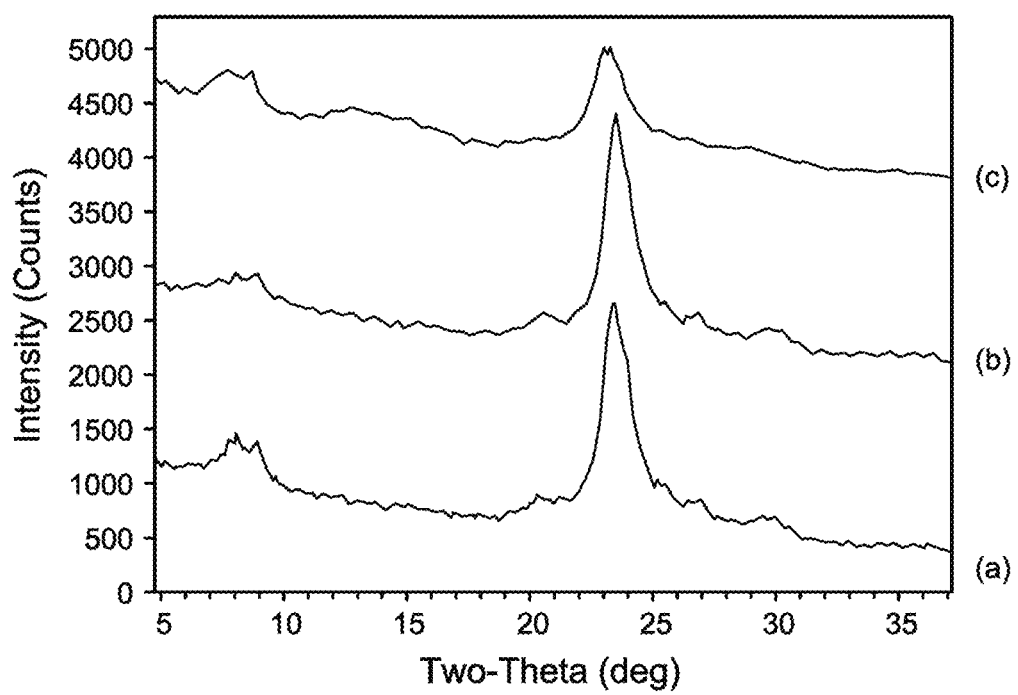
FIGS. 21 (a) to (c) show the X-ray diffraction patterns of the as-synthesized products of Examples 28, 29 and 31, respectively.

The process of Example 23 was repeated except the reaction was carried out at 110° C. for 6 days. FIG. 21(a) shows the powder XRD pattern of the product.

Example 29: Synthesis of ZSM-5 with the C5 Diquat of N-pentylpyrrolidine

The process of Example 24 was repeated except the reaction was carried out at 110° C. for 6 days. FIG. 21(b) shows the powder XRD of the product.

Example 30: Synthesis of ZSM-5 with the C5 Diquat of N-pentylpyrrolidine

A solution was prepared by mixing 3.95 g of a hydroxide solution of the C5 diquat of N-pentylpyrrolidine ([OH]=0.76 mmol/g) with 2.63 g 1 N KOH and 0.90 g deionized water inside a Teflon liner for a 23-mL steel Parr autoclave. 0.022 g SpectrAl fumed alumina (Cabot) was mixed into the solution to create a uniform suspension. The liner was then capped, sealed inside the 23-mL autoclave, and heated at 160° C. under tumbling conditions (~50 rpm) inside a convection oven for about 30 minutes in order to dissolve most of the alumina. The reactor was then cooled and 2.05 g Ludox AS-40 and 0.092 g metakaolin was then mixed into the solution. The liner was then capped, sealed inside the 23-mL autoclave, and heated at 130° C. under tumbling conditions (~50 rpm) inside a convection oven for 22 days. The solids were then isolated by filtering through a Buchner funnel, washing with deionized water, and drying in an oven at 100° C. Powder XRD showed the product to be ultra small crystal ZSM-5.

Example 31: Synthesis of ZSM-5 with the C5 Diquat of N-pentylpyrrolidine

The process of Example 30 was repeated except that only 0.015 g fumed alumina and 0.097 g metakaolin were used and the reaction was carried out for 15 days. FIG. 21(c) shows the powder XRD pattern. The broad hump from 10 to 15 degrees two theta is due to the plastic sample holder used for the powder XRD measurement.

While the present invention has been described and illustrated by reference to particular embodiments, those of ordinary skill in the art will appreciate that the invention lends itself to variations not necessarily illustrated herein.

For this reason, then, reference should be made solely to the appended claims for purposes of determining the true scope of the present invention.

The invention claimed is:

1. A process for producing a molecular sieve having the structure of ZSM-5, the process comprising:

(i) preparing a synthesis mixture capable of forming said molecular sieve, said synthesis mixture comprising a source of an alkali or alkaline earth metal (M), a source of an oxide of a tetravalent element Y, optionally a source of a trivalent element X, water, and a directing agent (Q) comprising one or more of 1,4-bis(N-pentylpyrrolidinium)butane dications, 1,5-bis(N-pentylpyrrolidinium)pentane dications, and 1,6-bis(N-pentylpyrrolidinium)hexane dications, and said synthesis mixture having a composition, in terms of mole ratios, within the following ranges:

| | |
|---|---|
| $YO_2/X_2O_3$ | at least 20; |
| $H_2O/YO_2$ | 10 to 60; |
| $OH^-/YO_2$ | 0.20 to 0.60; |
| $M/YO_2$ | 0.05 to 0.40; and |
| $Q/YO_2$ | 0.05 to 0.20; |

(ii) heating said synthesis mixture under crystallization conditions, including a temperature of from 80° C. to 200° C., and a time from 1 day to 21 days, until crystals of said molecular sieve are formed; and (iii) recovering said molecular sieve from step (ii), wherein (a) 1,4-bis(N-pentylpyrrolidinium)butane dications which can be represented by the following formula:

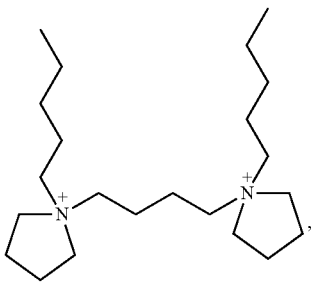

(b) 1,5-bis(N-pentylpyrrolidinium)pentane dications can be represented by the following formula:

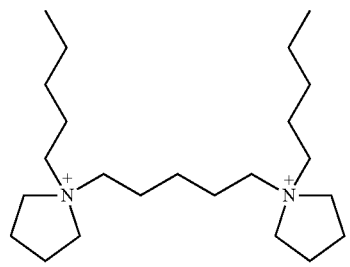

and (c) 1,6-bis(N-pentylpyrrolidinium)hexane dications can be represented by the following formula:

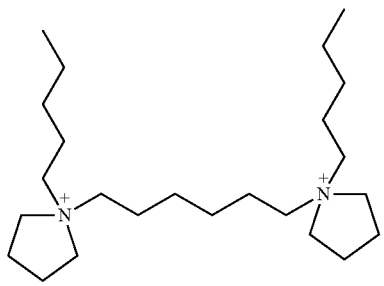

wherein said tetravalent element Y comprises silicon, and said trivalent element X comprises aluminum.

2. The process of claim 1, wherein said synthesis mixture has a composition, in terms of mole ratios, within the following ranges:

| | |
|---|---|
| $YO_2/X_2O_3$ | at least 24; |
| $H_2O/YO_2$ | 20 to 50; |
| $OH^-/YO_2$ | 0.25 to 0.50; |
| $M/YO_2$ | 0.1 to 0.40; and |
| $Q/YO_2$ | 0.05 to 0.20. |

3. The process of claim 1, wherein said synthesis mixture also contains seeds.

4. The process of claim 3, wherein said synthesis mixture comprises from about 0.01 ppm by weight to about 10,000 ppm by weight of seeds.

5. The process of claim 3, wherein said synthesis mixture comprises from about 100 ppm by weight to about 5,000 ppm by weight of seeds.

6. The process of claim 3, wherein said seeds comprise a crystalline material having the structure of ZSM-5.

7. The process of claim 1 and further comprising the step of removing at least part of said directing agent from the molecular sieve crystals recovered in step (iii).

* * * * *